United States Patent
Nemoto et al.

(10) Patent No.: US 9,889,447 B2
(45) Date of Patent: Feb. 13, 2018

(54) REAGENT SUPPLYING DEVICE

(71) Applicants: SEKISUI MEDICAL CO., LTD., Chuo-ku (JP); SEKISUI TECHNO MOLDING CO., LTD., Minato-ku (JP)

(72) Inventors: Yuriko Nemoto, Chuo-ku (JP); Hiroaki Taira, Chuo-ku (JP); Takuya Yotani, Chuo-ku (JP); Satoru Tominaga, Minato-ku (JP)

(73) Assignees: SEKISUI MEDICAL CO., LTD., Chuo-ku (JP); SEKISUI TECHNO MOLDING CO., LTD., Minato-ku (JP)

( * ) Notice: Subject to any disclaimer, the term of this patent is extended or adjusted under 35 U.S.C. 154(b) by 0 days.

(21) Appl. No.: 14/908,073

(22) PCT Filed: Jul. 25, 2014

(86) PCT No.: PCT/JP2014/069704
§ 371 (c)(1),
(2) Date: Jan. 27, 2016

(87) PCT Pub. No.: WO2015/012391
PCT Pub. Date: Jan. 29, 2015

(65) Prior Publication Data
US 2016/0184826 A1 Jun. 30, 2016

(30) Foreign Application Priority Data
Jul. 26, 2013 (JP) .................................. 2013-156180

(51) Int. Cl.
*A61J 1/06* (2006.01)
*B01L 3/00* (2006.01)
(Continued)

(52) U.S. Cl.
CPC ................. *B01L 3/52* (2013.01); *B01L 3/523* (2013.01); *B01L 3/527* (2013.01); *G01N 30/02* (2013.01);
(Continued)

(58) Field of Classification Search
CPC ... A61J 1/06; B01L 3/00; G01N 21/00; G01N 1/10
(Continued)

(56) References Cited

U.S. PATENT DOCUMENTS 5,665,315 A 9/1997 Robert et al.
6,818,185 B1 * 11/2004 Petersen et al. .............. 422/547
(Continued)

FOREIGN PATENT DOCUMENTS

CN 101360609 2/2009
CN 102470365 5/2012
(Continued)

OTHER PUBLICATIONS

Office Action dated Aug. 2, 2016, in Chinese Patent Application No. 201480042007.8.
(Continued)

*Primary Examiner* — Brian J Sines
(74) *Attorney, Agent, or Firm* — Oblon, McClelland, Maier & Neustadt, L.L.P.

(57) ABSTRACT

Provided are a reagent supply method and device capable of using up a reagent in a container without a remnant to the extent possible, and supplying the reagent to an analysis device without mixing air bubbles even when the remaining amount of the reagent is extremely small. The reagent supply device includes: at least one reagent container including: a container body for storing a liquid reagent; and a reagent supply port arranged on the container body; and a support member for supporting the at least one reagent
(Continued)

container so that the reagent supply port is positioned on a lower side of the container body. The reagent supply port is sealed by a plug including at least one nozzle penetration portion. The at least one nozzle penetration portion is formed of a material having a Shore hardness of from A5° to A90°.

15 Claims, 3 Drawing Sheets

(51) Int. Cl.
  *G01N 21/00* (2006.01)
  *G01N 1/10* (2006.01)
  *G01N 35/10* (2006.01)
  *G01N 30/02* (2006.01)
  *G01N 30/88* (2006.01)

(52) U.S. Cl.
  CPC .... *G01N 35/1002* (2013.01); *B01L 2200/025* (2013.01); *B01L 2200/026* (2013.01); *B01L 2200/16* (2013.01); *B01L 2300/044* (2013.01); *B01L 2300/0609* (2013.01); *B01L 2300/0672* (2013.01); *B01L 2300/0809* (2013.01); *B01L 2300/12* (2013.01); *B01L 2300/123* (2013.01); *G01N 35/1079* (2013.01); *G01N 2030/027* (2013.01); *G01N 2030/8822* (2013.01)

(58) Field of Classification Search
  USPC ........ 422/50, 68.1, 417, 547, 552, 554, 560, 422/561, 570; 436/43, 180
  See application file for complete search history.

(56) References Cited

U.S. PATENT DOCUMENTS

| | | | |
|---|---|---|---|
| 2006/0060535 A1* | 3/2006 | Ellis | G01N 30/6026 210/656 |
| 2007/0282293 A1 | 12/2007 | Janus | |
| 2009/0281930 A1 | 11/2009 | Sakagami | |
| 2010/0310426 A1* | 12/2010 | Campbell et al. | 422/100 |
| 2011/0085746 A1 | 4/2011 | Wong et al. | |
| 2011/0240501 A1 | 10/2011 | Janus | |
| 2012/0012466 A1* | 1/2012 | Sperry et al. | 205/334 |
| 2014/0234949 A1* | 8/2014 | Wasson et al. | 435/287.2 |

FOREIGN PATENT DOCUMENTS

| | | |
|---|---|---|
| EP | 0 192 794 A1 | 9/1986 |
| EP | 0 697 248 A1 | 2/1996 |
| JP | 60-41852 U | 3/1985 |
| JP | 8-105900 A | 4/1996 |
| JP | 9-113494 A | 5/1997 |
| JP | 10-10105 A | 1/1998 |
| JP | 2007-71549 A | 3/2007 |
| JP | 2008-155593 A | 7/2008 |
| JP | 2008-180640 A | 8/2008 |
| WO | WO 99/67646 A1 | 12/1999 |

OTHER PUBLICATIONS

International Search Report dated Oct. 28, 2014 in PCT/JP2014/069704 (with English language translation).
"Handbook of High Performance Liquid Chromatography" edited by Kanto Branch of the Japan Society for Analytical Chemistry, 2$^{nd}$ Edition, Published Mar. 25, 2000, 8 Pages (with Partial English language translation).
Extended European Search Report dated Jan. 30, 2017 in Patent Application No. 14830223.5.

* cited by examiner

REAGENT SUPPLYING DEVICE

FIELD OF THE INVENTION

The present invention relates to a method and device for supplying a reagent to a sample analysis device, and to a method of analyzing a sample using the reagent supply method.

BACKGROUND OF THE INVENTION

Separation analysis methods for a sample, such as liquid chromatography, are generally used for analysis or test in the fields of organic chemistry, biochemistry, medical science, or the like. In those separation analysis methods, there are used various reagents such as an eluent for separating the sample, a washing solution for washing a column or a flow channel for the reagent, a diluent for diluting the sample, and a washing diluent for both washing and diluting. Those reagents are conventionally provided under a state of being filled in a bottle made of glass or a resin. However, when the reagent is filled in the bottle made of glass or a resin, there is a problem in that air space is generated in the bottle along with consumption of the reagent so that the reagent is concentrated due to evaporation or condensation of volatile components. Thus, in Patent Literature 1, there is disclosed a flexible reagent bag obtained by processing a lamination of a resin layer and an aluminum foil layer into a bag-like shape as a container that is capable of reducing its volume along with the reduction in the amount of the reagent and is also excellent in preservability of the reagent.

As described in Non Patent Literature 1, the above-mentioned reagent filled in the container is sucked up through a suction nozzle or the like inserted downward into the container from an opening formed on an upper of the container, and is supplied to the analysis device. However, when the remaining amount of the reagent in the container is smaller, the reagent is hardly sucked through the suction nozzle, or air bubbles may be generated due to air sucked together with the reagent. Thus, the reagent cannot be supplied in an appropriate amount, with the result that accurate analysis cannot be performed. As a method for avoiding the suction of the air during the suction of the reagent, there is known a method as disclosed in Patent Literature 2, which involves managing a usage amount of the reagent, and completing the use of the reagent in the container under a state in which the reagent in an amount sufficient for avoiding the suction of the air is left in the container. However, in this method, the reagent remaining in the container needs to be discarded, which is not economical. Some of the reagents to be used in the separation analysis are expensive, such as a dedicated eluent put on sale with a liquid chromatograph, and hence there is a demand to use up the reagent without discarding the reagent to the extent possible. In Patent Literature 3, there is disclosed a reagent container capable of using up the reagent without sucking the air even when the remaining amount of the reagent is extremely small, in which an inclination or a recess is formed on a bottom, and a distal end of a reagent suction nozzle is arranged on a lowermost portion of the inclination or in the recess. However, the reagent container also has a problem in that the suction nozzle is long so that air bubbles are easily generated due to reduction in pressure in the nozzle during the suction of the reagent.

When the flexible reagent bag, such as a bag made of a resin, is set in the analysis device, the following procedure needs to be taken as a general procedure. A cap is removed from the reagent bag, and the bag is squeezed to push out internal air. After that, the reagent suction nozzle is inserted into the reagent container, and then a cap provided to the reagent suction nozzle is tightened to hermetically seal the bag. However, when the air cannot be pushed out sufficiently from the container in the above-mentioned procedure, the air space is generated in the container, which may cause the above-mentioned problem about the concentration of the reagent. Further, the above-mentioned procedure requires a skill of a user. In addition, when mounting or removing the cap or pushing out the air from the bag, the user may touch the reagent or contamination of the reagent may occur.

CITATION LIST

Patent Literature

[PTL 1] JP-A-2008-155593
[PTL 2] JP-A-2008-180640
[PTL 3] JP-A-10-10105

Non Patent Literature

[NPL 1] Handbook of High Performance Liquid Chromatography, edited by the Kanto Branch of the Japan Society for Analytical Chemistry, 2nd edition, p. 141, published in Mar. 25, 2000, Maruzen

SUMMARY OF THE INVENTION

Problem to be Solved by the Invention

It is an object of the present invention to provide a reagent supply method and device capable of using up a reagent in a reagent container without a remnant to the extent possible, and supplying the reagent to an analysis device without mixing an air bubble even when the remaining amount of the reagent is extremely small.

Means for Solving Problem

In order to achieve the above-mentioned object, the inventors of the present invention found out that, by causing the reagent to flow in a downward direction out of the reagent container having a reagent supply port arranged on a lower side of a container body, and feeding the reagent flowing out of the reagent container to the analysis device, the reagent in the reagent container was able to be used up without a remnant to the extent possible, and an accurate amount of the reagent was able to be supplied to the analysis device without mixing the air bubble even when the remaining amount of the reagent was extremely small. Further, the inventors of the present invention found out that, by manufacturing the reagent supply port using a material having a predetermined hardness, it was possible to provide a reagent container excellent in durability without liquid leakage or contamination of the reagent in the container even over long-term use.

That is, according to one embodiment of the present invention, there is provided a reagent supply device, comprising:
  at least one reagent container comprising:
  a container body for storing a liquid reagent; and
  a reagent supply port arranged on the container body; and
  a support member for supporting the at least one reagent container, so that the reagent supply port is positioned on a lower side of the container body, wherein the reagent supply port comprises at least one nozzle penetration portion, the at least one nozzle penetration portion is formed of a material having a Shore hardness of from A5° to A90°.

Further, according to one embodiment of the present invention, there is provided a sample analysis device, comprising:

the reagent supply device described above; and
a sample analysis unit.

Further, according to one embodiment of the present invention, there is provided a method of supplying a reagent to a sample analysis unit, the method comprising:

setting at least one reagent container,
the at least one reagent container comprising a container body for storing a liquid reagent, and a reagent supply port arranged on a lower side of the container body, the reagent supply port comprising at least one nozzle penetration portion, the at least one nozzle penetration portion being formed of a material having a Shore hardness of from A5° to A90°;

causing the liquid reagent to flow out of the reagent container in a downward direction through a nozzle inserted into the reagent container through the nozzle penetration portion; and feeding the liquid reagent to the sample analysis unit.

Further, according to one embodiment of the present invention, there is provided a method of analyzing a sample, the method comprising:

setting at least one reagent container,
the at least one reagent container comprising a container body for storing a liquid reagent, and a reagent supply port arranged on a lower side of the container body, the reagent supply port comprising at least one nozzle penetration portion, the at least one nozzle penetration portion being formed of a material having a Shore hardness of from A5° to A90°;

causing the liquid reagent to flow out of the reagent container in a downward direction through a nozzle inserted into the reagent container through the nozzle penetration portion, and feeding the liquid reagent to a sample analysis unit; and processing or analyzing the sample using the fed liquid reagent.

Effect of the Invention

In the reagent supply device according to the present invention, the reagent supply port is arranged on the lower side of the container body, and hence the liquid reagent can be caused to flow out of the container through the supply port in the downward direction of the container. Thus, it is unnecessary to suck up the reagent by a long nozzle. Therefore, according to the reagent supply device of the present invention, the reagent in the container can be used up without remnants, and even when the remaining amount of the reagent is extremely small, the air bubbles are not mixed into the reagent. The description "using up the reagent without remnants" herein encompasses a case where the remaining amount of the reagent at the end of the use of the reagent is smaller in the present invention as compared with the conventional reagent supply method. Further, in the reagent supply device according to the present invention, the nozzle is caused to penetrate the hermetically-sealed reagent container so that the reagent is supplied thereinto, thereby being capable of preventing the contamination of the reagent or the contact between a user and the reagent, which may be caused when opening the container. In addition, the nozzle penetration portion is formed of the material having a high elastic limit, and hence even when using for a long period of time under a state in which the nozzle is caused to penetrate the nozzle penetration portion, the reagent does not leak from the penetration portion, and hence the reagent supply device is durable over the long-term use. Further, a flexible container is used as the reagent container for storing the liquid reagent in the reagent supply device according to the present invention. Thus, even when the reagent is used to be reduced in the amount, the container is deflated to prevent formation of large air space in the container. Thus, evaporation or dew condensation of volatile components is suppressed, thereby being capable of preventing concentration of the liquid reagent remaining in the container. Therefore, the present invention provides accurate and economical means for supplying an appropriate amount of the reagent to the analysis device.

MODE FOR CARRYING OUT OF THE INVENTION

Figure 1:
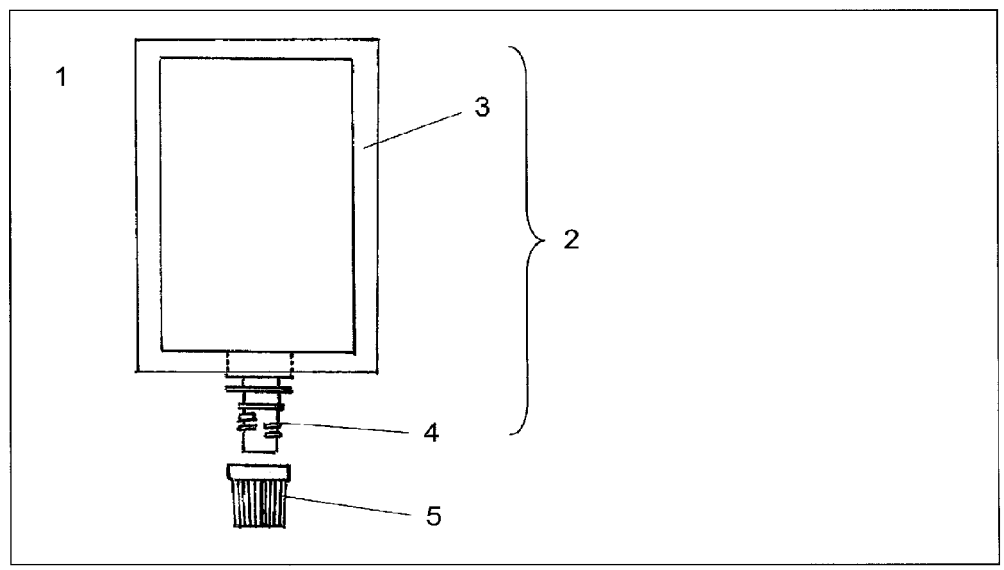
FIG. 1 is a schematic view of a reagent container.

A reagent supply device according to the present invention may be used for supplying a reagent to various sample analysis units such as a liquid chromatograph or a blood test device. Reagents that may be supplied by the reagent supply device according to the present invention are not particularly limited in the number or kinds as long as the reagent is a liquid reagent. The reagent supply device according to the present invention can supply one reagent, or two, three or more liquid reagents, depending on the kinds or the number of the reagents required for desired analysis. As the reagents to be supplied by the reagent supply device according to the present invention, there are given, for example, a reagent for liquid chromatography, a reagent for analysis of biological samples such as blood, and a reagent for clinical laboratory test.

1. Reagent Container

The reagent supply device according to the present invention comprises one or a plurality of reagent containers. The respective reagent containers store the same kind or different kinds of liquid reagents, and the number of the reagent containers or kinds of the reagents to be stored may be selected, depending on an analysis method in which the reagent is used. The reagent containers each comprise a container body for storing the liquid reagent, and a reagent supply port arranged on a lower side of the container body.

A material of the container body of the reagent container is not particularly limited, and there are given, for example, glass, a metal, a resin, or a lamination thereof. When a reagent which is easily deteriorated by light is stored, it is desired to use a light-resistant material, such as a metal, colored glass, or a colored resin. Further, it is preferred that the container body is a flexible container formed of a material having flexibility. With use of the flexible container, the container is deflated along with consumption of the liquid reagent in the container. Thus, formation of large air space in the container can be prevented even when the remaining amount of the reagent is reduced. As a result, concentration of the reagent that may be caused due to evaporation of volatile components from the liquid reagent or condensation of the volatile components in the container can be prevented. As the flexible container, there are given, for example, a bag made of a resin, and a bag formed by a lamination of a resin layer and a metal layer or the like. As a more specific example, a bag manufactured in the following manner is given. A lamination is manufactured by laminating, in the order from an innermost layer, a polyolefin layer, a polyester-based resin layer or a polyester-based resin layer having an inorganic compound vapor-deposited thereon, an aluminum foil layer, or the like. The obtained lamination is molded into a bag-like shape, and then, an outlet portion is bonded to the lamination through heat sealing or the like. It is preferred that the outlet portion be formed of a material having rigidity and coupled to the reagent supply port through threaded engagement, fitting, meshing, or the like. Further, in order to maintain the strength of the container, thicknesses of constituent layers, such as the above-mentioned polyolefin layer, may be increased to the extent that the quality of the reagent to be stored may not be adversely affected, or a reinforcement material such as a polyamide-based resin or a polyester-based resin may be used as the material. The flexible container may have a shape capable of standing by itself. Further, in order to enhance operability, a handle or the like may be provided as necessary.

The reagent supply device according to the present invention may comprise a housing for accommodating the above-mentioned one or plurality of reagent containers. The housing has a function to protect the reagent container, and also has a function as a guide for arranging each reagent container at an appropriate position with respect to the sample analysis unit, so that an appropriate reagent is supplied to the analysis unit. For example, the housing is a reagent cartridge to be set in an analysis device comprising the sample analysis unit. As the shape (outer appearance) of the housing, both a symmetric shape and an asymmetric shape may be employed. When the asymmetric shape is employed, a direction of the cartridge to be set in the analysis device can be defined, and hence the plurality of reagent containers in the cartridge can be connected to the analysis device in appropriate arrangement. Further, for example, the reagent containers may be arranged in the housing uniformly-spaced or non-uniformly-spaced. The reagent containers may be accommodated in the housing in the non-uniform-spaced arrangement. Meanwhile, a support member is formed in the analysis device comprising the sample analysis unit, for supporting the reagent containers and the housing in the corresponding non-uniform-spaced arrangement. Thus, the housing can be set in conformity with the shape of the support member, so that the reagent containers can be connected to the analysis device in appropriate arrangement.

As a material of the housing, there are given, for example, polypropylene, polyethylene, nylon, polyethylene terephthalate, polyacetal, polyamide, polybutylene terephthalate, an ABS resin, polystyrene, an AS resin, and a polymethyl methacrylate resin. A material obtained by mixing those resins may also be given.

2. Support Member

The reagent supply device according to the present invention further comprises the support member for supporting the above-mentioned reagent container. The support member may comprise one or a plurality of members for separately supporting the one or the plurality of reagent containers, or may be a single member for collectively supporting the one or the plurality of reagent containers. Alternatively, the support member may support the reagent container by supporting the housing accommodating the above-mentioned reagent container. In any case, each of the reagent containers is arranged by the support member so that the reagent supply port is positioned on the lower side of the reagent container body. Therefore, in the reagent supply device according to the present invention, the liquid reagent in the reagent container is caused to flow out of the container in a downward direction at the lower side of the container. Thus, conventional suction of the liquid reagent is unnecessary, thereby preventing mixing of air bubbles into the liquid reagent that may be caused due to the suction. Therefore, the reagent supply device according to the present invention does not require an operation of removing air from the reagent container before use when the flexible container is used as the reagent container, which is required in the conventional procedure of setting the reagent container. In addition, the reagent in the container can be used up.

3. Reagent Supply Port

The reagent supply port of the above-mentioned reagent container is not opened in an unused state, and comprises one or a plurality of nozzle penetration portions for allowing a nozzle to penetrate. For example, the reagent supply port is a plug mounted to the reagent container, and the plug comprises one or a plurality of nozzle penetration portions. One end of the nozzle penetration portion is an outward-facing surface facing the outside of the container, and an end opposed thereto is an inward-facing surface facing the inside of the container. The nozzle inserted into the outward-facing surface is capable of penetrating the inward-facing surface. In this manner, the nozzle penetrates the plug for closing the reagent supply port, and the liquid reagent in the container is supplied to the outside through the nozzle. Therefore, in the reagent supply device according to the present invention, the nozzle is caused to penetrate the hermetically-sealed reagent container so that the reagent is supplied without opening the reagent container, thereby being capable of preventing contamination of the reagent or contact between a user and the reagent, which may be caused when opening the container.

A shape of the nozzle penetration portion is not particularly limited as long as the liquid does not leak from the penetration portion even when the reagent supply device is left for a long period of time under a state in which the nozzle is caused to penetrate the penetration portion. It is preferred that the nozzle penetration portion has a shape such as a cylindrical shape that allows the nozzle to equally receive a pressure. Further, it is desired that the nozzle penetration portion is formed of a material that may cause no liquid leakage and give no adverse influence to the quality of the reagent with less elution into the reagent when the nozzle penetration portion is brought into contact with the stored liquid reagent. Moreover, it is preferred that the nozzle penetration portion is formed of a material that may cause no liquid leakage from the penetration portion even when it is left for a long period of time, for example, for three months or more under the state in which the nozzle is caused to penetrate the penetration portion. For example, it is preferred that the nozzle penetration portion is formed of a material having a Shore hardness of from A5° to A90°. The Shore hardness is preferably A60° or less, more preferably A50° or less. It is preferred that a lower limit of the Shore hardness is A5° in view of reduction in stickiness. Examples of the material having such hardness may include synthetic rubber (such as isoprene rubber, an isoprene-isobutylene copolymer, butyl rubber, butadiene rubber, an ethylene-propylene copolymer, an ethylene-propylene-third component copolymer, urethane rubber, or silicone rubber), natural rubber, and an elastomer. Of those, preferred examples thereof may include an olefin-based elastomer and a styrene-based elastomer or the like. A crosslinking accelerator may be mixed into the material. Further, the following substance may appropriately be blended into the material: an inorganic filler, such as calcined clay, silica, a metal oxide, or carbon black; or oil or the like. Note that, the Shore hardness may be measured in accordance with the Shore hardness test defined in the Japanese Industrial Standards (JIS) Z 2246.

The plug may entirely comprise the nozzle penetration portion through which the nozzle may penetrate. It is preferred that the plug comprise a plug body formed of a material having such rigidity that the nozzle may not penetrate therethrough at least in a periphery of the plug body. As the material of the plug body, a material having a Rockwell hardness of from R80 to R110 is given. Note that, the Rockwell hardness may be measured in accordance with the Rockwell hardness test defined in the Japanese Industrial Standards (JIS) G 0202. Further, it is preferred that the material of the plug body is a material that is excellent in adhesiveness with a material of the container body of the reagent container and may cause no liquid leakage. Examples of such material may include a polyolefin-based resin and a Teflon (trademark)-based material. Of those, an additive-free grade polyolefin-based resin or an additive-free Teflon (trademark)-based material is preferred from the viewpoint of reducing the elution when the material is brought into contact with the stored reagent. Polypropylene or polyethylene is preferred as the polyolefin-based resin. Of those, high-density polyethylene, a mixture of polypropylene and low-density polyethylene, or the like is more preferred from the viewpoint of maintaining the strength and the water vapor barrier property of the plug.

The nozzle penetration portion and the plug body have a structure that allows close contact therebetween to prevent the leakage of the reagent from the container or the contamination. For example, the nozzle penetration portion is connected to the plug body each other at their flanges, so that the nozzle penetration portion is contracted, thereby further enhancing close-contact property. Further, through addition of a compatibilizer, such as a low-molecular-weight olefin (such as an acid-modified polyolefin-based resin) or a block copolymer, to a material of the nozzle penetration portion, the close-contact property between the nozzle penetration portion and the plug body can further be enhanced. The plug body and the nozzle penetration portion may be manufactured by a known method such as extrusion molding, injection molding and blow molding, respectively. In the case of the injection molding, insert molding and double injection molding are suitable.

In order to avoid the contamination of the reagent, the nozzle penetration portion may not be exposed to an external environment until the nozzle is inserted. Therefore, the plug of the reagent container is sealed to cover the nozzle penetration portion, or the plug of the reagent container may be provided under a state of being covered by a cover or a cap, which is removable in use.

4. Nozzle

The nozzle to be inserted into the nozzle penetration portion has a material and a shape that may penetrate the nozzle penetration portion having the above-mentioned Shore hardness. The shape of the nozzle is not particularly limited, and is preferred to be a hollow needle, and is more preferred to be a needle sealed at its acute end with a lateral hole, or a needle polished into a lancet point shape at its distal end, a needle polished into a semi-lancet point shape at its distal end, or a needle polished into a back-cut point shape at its distal end or the like. The shape of the acute end of the nozzle is not particularly limited as long as the nozzle may penetrate the nozzle penetration portion, and a cone shape, a triangular pyramid shape, and a quadrangular pyramid shape are given as examples. It is preferred that the material of the nozzle is a metal, a resin, a ceramic, or the like because of the penetrability of the nozzle penetration portion and the elution property of the reagent. In order to eliminate remnants of the reagent, it is desired that an upper end of the nozzle is held at a position as close to a bottom of the container body as possible after the nozzle penetrates the nozzle penetration portion and is inserted into the container body. In the meantime, when a distance of inserting the nozzle is short, the nozzle may drop off. Therefore, it is preferred that the reagent supply device according to the present invention comprises a guide or a stopper for controlling the distance of inserting the nozzle into the nozzle penetration portion.

It is preferred that the nozzle is provided in the reagent supply device according to the present invention. Further, a tube or a flow channel may be coupled to the nozzle, for establishing fluid connection between the reagent container and a liquid feeder or a sample analysis unit described later, so that the liquid reagent is fed to the liquid feeder or the sample analysis unit. In one embodiment, the above-mentioned support member comprises one or a plurality of nozzles, and each nozzle is arranged, so that the acute end is directed in an upward direction at a position where the nozzle may penetrate the nozzle penetration portion of each reagent container when the support member supports the reagent container. Thus, when the reagent container is set on the support member, the nozzles are respectively inserted into the nozzle penetration portions of the reagent containers at the same time, and the insertion distance for each of the nozzles is controlled, thereby preventing the nozzles from entering the containers excessively deeply or dropping off the containers. Further, the tube connected to the liquid feeder or the sample analysis unit in advance is coupled to each of the nozzles. When the nozzles are each inserted into the reagent container, the reagent can be supplied to the sample analysis unit.

5. Liquid-Feeding System

In the reagent supply device according to the present invention, the reagent supply port is arranged on the lower side of the reagent container body, and hence the reagent in the container body is caused to flow out of the container in a downward direction through the nozzle set in the nozzle penetration portion of the reagent supply port. The liquid reagent flowing out through the nozzle is supplied to the sample analysis unit for analyzing a sample using the reagent. Therefore, in one preferred embodiment, the reagent container of the reagent supply device according to the present invention is arranged at a position higher than the sample analysis unit to which the reagent is to be supplied, and the reagent is supplied to the sample analysis unit utilizing a pressure caused when the liquid reagent is caused to flow out while falling down. In another preferred embodiment, the reagent supply device according to the present invention is used in combination with the liquid feeder such as a pump or a valve for transporting the liquid reagent actively, to thereby supply the reagent to the sample analysis unit. The liquid feeder may control the supplies of the plurality of reagents in common. It is desired that the liquid feeder is provided independently for each liquid reagent to be supplied from the reagent supply device in order to supply the plurality of reagents required for the analysis at an appropriate timing. Both the configurations may be combined with each other, so that the reagent is fed due to the pressure caused when the liquid reagent is caused to flow out while falling down and the driving force of the liquid feeder. Therefore, in a further embodiment, the reagent supply device according to the present invention further comprises one or a plurality of liquid feeders.

6. Sample Analysis Device

The reagent supply device according to the present invention may be an independent device, and may also be a reagent supply unit constituting a sample analysis device for analyzing the sample using the reagent supplied from the device. The sample analysis device comprises the reagent supply unit corresponding to the reagent supply device according to the present invention, and the sample analysis unit for processing or analyzing the sample using the supplied liquid reagent, and comprises the liquid feeder as necessary. The sample analysis device may further comprise various components such as a power source and an operation portion, which are required for the analysis. As the sample analysis device provided by the present invention, a liquid chromatograph, the blood sample analysis device, a clinical laboratory test device are given as examples.

In one embodiment of the sample analysis device, a set of the liquid reagents, which are required for the analysis in the device, is provided in the form of a case or a housing accommodating the one or the plurality of reagent containers including the respective reagents. The reagent supply unit comprises the support member for stably supporting the case or the housing. When the case or the housing is set on the reagent supply unit, the reagent supply port of the reagent container in the case or the housing is arranged on the lower side of the reagent container due to the function of the support member. The reagent supply unit further comprises the nozzles respectively corresponding to the nozzle penetration portions of the reagent supply ports of the reagent containers in the case or the housing. When the nozzles are respectively inserted into the nozzle penetration portions, the liquid reagents in the reagent containers can be supplied to the outside. It is preferred that the support member and the nozzles are integrally formed with each other. When the case or the housing is set on the reagent supply unit, the reagent supply ports are arranged to be directed in a downward direction and the nozzles are arranged at positions corresponding to the nozzle penetration portions so that the nozzles are caused to penetrate the nozzle penetration portions. Thus, the liquid reagents in the reagent containers can be supplied to the outside. Accordingly, the fluid connection between the reagent container and the sample analysis unit is established through the nozzle, optionally through the liquid feeder. Thus, the required reagent is supplied from the reagent supply unit to the sample analysis unit. When the fluid connection is established and the liquid feeder is provided independently for each of the reagents, a required reagent can be supplied to the sample analysis unit in a required amount at a required timing. In a preferred embodiment of the sample analysis device, the reagent supply unit is arranged at a position higher than the sample analysis unit. The reagent supply device according to the present invention is incorporated into the sample analysis device, and hence it is unnecessary to provide a long flow channel for sucking up the reagent from the container and supplying the reagent to the analysis unit unlike the conventional analysis device, thereby being capable of preventing generation of an air bubble. The nozzle penetration portion of the reagent supply device according to the present invention is excellent in durability, and hence it is generally unnecessary to replace the reagent container until the reagent in the container is used up as long as the same analysis is continued. The sample analysis device using the reagent supply device according to the present invention is supplied with an accurate amount of the reagent even when the remaining amount of the reagent is extremely small, thereby being capable of performing highly-accurate analysis all the time.

7. Liquid Chromatograph

As a specific example of the sample analysis device incorporating the reagent supply device according to the present invention, a blood sample analysis device using liquid chromatography is described. The analysis device is a device using blood as a sample, for measuring an amount of a hemoglobin component (such as hemoglobin A1c) in the blood by separating and detecting the hemoglobin component. The analysis device may be used, for example, as diabetic testing equipment. This analysis uses at least one liquid reagents selected from the group consisting of a solution for hemolyzing or diluting a blood sample, and a washing solution for washing a flow channel for the sample, an eluent for separating components to be detected from the sample solution, or the like. As to those reagents, one reagent may be used for a plurality of applications, and, for example, the solution for hemolysis or dilution and the washing solution may be the same reagent. Alternatively, a plurality of different reagents may be used for one application, and for example, a plurality of reagents may be used for hemolysis or dilution for the sample, or the plurality of reagents may be used as the washing solution or the eluent. In one embodiment, there are used a reagent being the solution for hemolyzing or diluting a blood sample and being the washing solution for washing the flow channel for the sample (solution for hemolysis, dilution, and washing), and one or two or more eluents.

The at least one liquid reagents are respectively filled in different reagent containers. The reagent containers filled with the liquid reagents may have the same shape or capacity, and may have different shapes or capacities. It is preferred that each of the reagent containers has a size that allows a liquid reagent of approximately 100 mL to be filled therein. Each of the reagent containers also has a larger capacity of, for example, approximately 500 mL when a large amount of the reagent is required for analysis as in a case of using a large amount of the washing solution, the diluent, or the eluent.

The at least one liquid reagents may be provided in the form of a reagent kit accommodated in one housing. The reagent kit is set on the support member formed in an upper of a body of the blood sample analysis device, so that the reagent supply ports of the plurality of reagent containers accommodated in the reagent kit are directed in a downward direction. In one embodiment, the support member is recesses for supporting the reagent containers by entirely supporting the reagent kit, and comprises the nozzles at positions corresponding to the nozzle penetration portions of the plurality of reagent supply ports. When the reagent kit is set in the analysis device, the reagent supply ports are each arranged on the lower side of the reagent container, and the nozzles are each caused to penetrate the nozzle penetration portion of the reagent container to enter the container. Thus, the liquid reagent can be supplied to the analysis device. The blood sample analysis device comprises the liquid feeders such as the pumps and/or the valves, for controlling liquid feeding at portions on the flow channels for the respective liquid reagents. When the analysis device is activated, the liquid reagents are started to be fed so that the hemolysis and the dilution for the blood sample, the separation of the hemoglobin component from the diluted blood, and the washing of the flow channel are executed at an appropriate timing.

EXAMPLE

The embodiment of the present invention is more specifically described by way of example, and the present invention is not limited to those examples. Further, embodiments described in the figures for reference merely exemplify the present invention. It is needless to say that the present invention may encompass various improvements and modifications made by a person skilled in the art within the scope of claims in addition to the matters directly described in the embodiments.

Example 1

Reagent Supply Device (Manufacturing of Lamination)

A lamination was obtained by laminating an additive-free grade low-density polyethylene film (having a thickness of 130 μm), a polyethylene terephthalate film (having a thickness of 12 μm), a nylon film (having a thickness of 25 μm), aluminum foil (having a thickness of 15 μm), and a polyethylene terephthalate film (having a thickness of 12 μm) in the stated order. Note that, the low-density polyethylene film and the polyethylene terephthalate film were bonded through extrusion lamination of low-density polyethylene. Further, the polyethylene terephthalate film, the nylon film, the aluminum foil, and the polyethylene terephthalate film were bonded by a dry lamination method using linear high-molecular polyester as an adhesive.

(Reagent Container Body)

A flexible bag was manufactured using the obtained lamination so that the above-mentioned additive-free grade low-density polyethylene film is formed as an innermost layer. Next, an outlet portion (diameter of 1 cm) was manufactured by an injection molding of additive-free grade polyethylene, and the outlet portion was fused with heat to the above-mentioned bag. In this manner, the reagent container body was manufactured.

(Reagent Supply Port)

The plug body was manufactured using a mixed material of polypropylene and low-density polyethylene. The Rockwell hardness of the plug body was measured in accordance with JIS G 0202 using a Rockwell hardness testing machine. The nozzle penetration portion was manufactured using an olefin-based elastomer. The Shore hardness of the nozzle penetration portion was measured in accordance with JIS Z 2246 using a Shore hardness testing machine. The Rockwell hardness of the plug body fell within a range of from R80 to R90, and the Shore hardness of the nozzle penetration portion fell within a range of from A40° to A50°. The plug including the nozzle penetration portion was manufactured through double injection molding using a double injection molding device.

Figure 2:
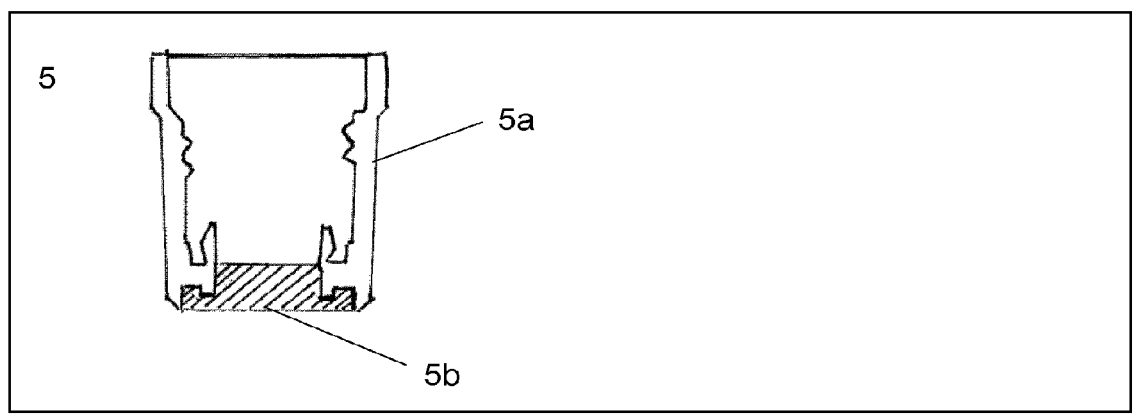
FIG. 2 is a schematic view of a cross-section of a reagent supply port.

FIG. 1 is a schematic view of one embodiment of a reagent container used in the present invention, which is manufactured in accordance with the above-mentioned procedure. A reagent container 1 includes a container body 2 having an outlet portion 4 fixed to a flexible bag 3, and a reagent supply port 5. FIG. 2 is a schematic view of a cross-section of the reagent supply port 5 illustrated in FIG. 1. The reagent supply port 5 is a plug including a plug body 5a and a nozzle penetration portion 5b, and is closed until the start of use of a reagent. When the reagent container 1 is directed so that the reagent supply port 5 is positioned on a lower side as illustrated in FIG. 1, the nozzle penetration portion 5b is arranged at a lower part of the reagent supply port 5 as illustrated in FIG. 2. The plug body 5a and the nozzle penetration portion 5b are held in close contact with each other to be joined at their flanges. Further, the outlet portion 4 of the container body and the reagent supply port 5 each have a screw thread so as to be threadedly engaged with each other. Thus, even when the reagent supply port 5 is directed in a downward direction, leakage of a liquid reagent from the reagent container 1 is prevented.

Figure 3:
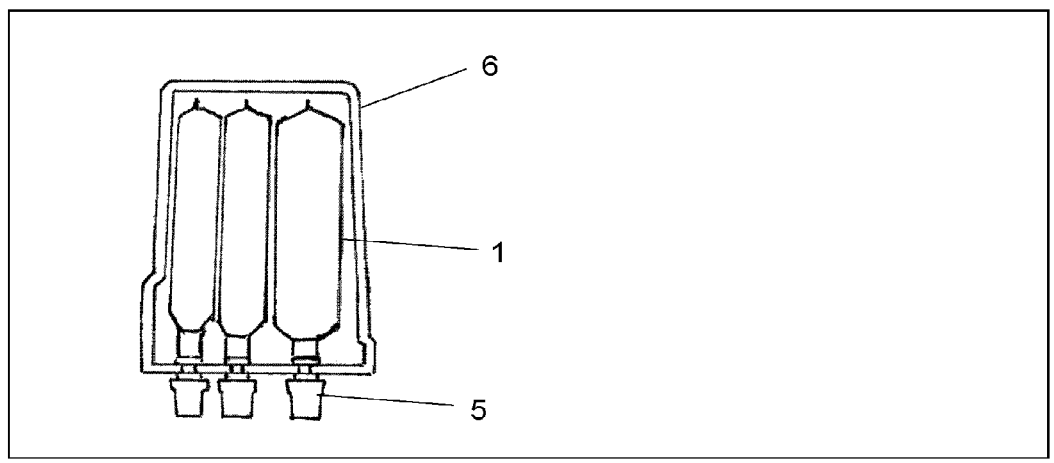
FIG. 3 is a schematic view of a cross-section of a housing accommodating the reagent containers.

FIG. 3 is a schematic view of a cross-section of one embodiment of a housing accommodating the reagent containers 1 illustrated in FIG. 1. The housing 6 illustrated in FIG. 3 accommodates a plurality of reagent containers 1 each having different capacities, and the plurality of reagent containers 1 are accommodated in the housing 6 in non-uniform-spaced arrangement. In the reagent containers 1 accommodated in the housing 6, the container body is accommodated inside the housing 6, while the reagent supply ports 5 are exposed to the outside so that nozzles are insertable through the reagent containers 1.

Figure 4:
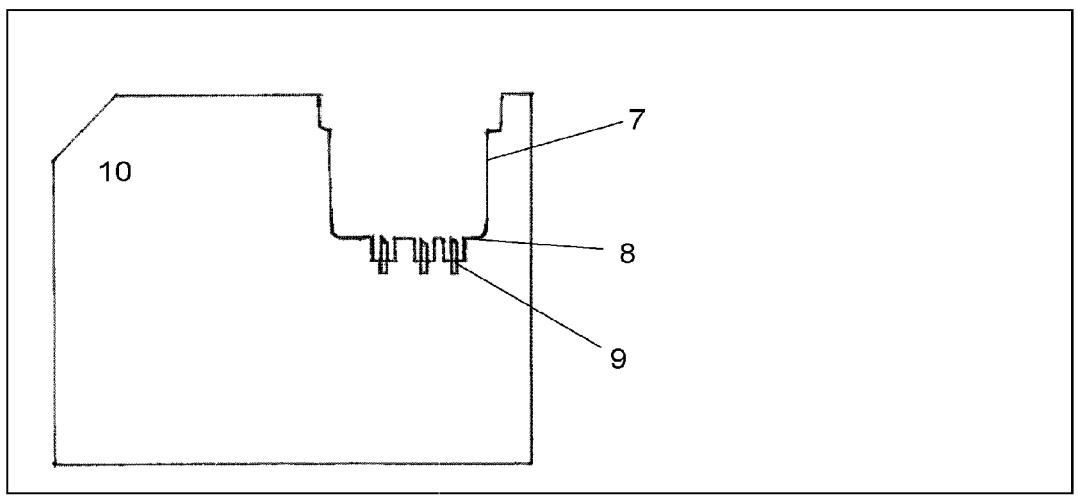
FIG. 4 is a schematic view of a support member for supporting the reagent containers.

FIG. 4 is a schematic view of one embodiment of a support member of the reagent supply device according to the present invention, for supporting the reagent containers. In FIG. 4, a support member 7 is formed on a body 10 of an analysis device for an analysis using the reagent supplied from the reagent supply device of the present invention. The support member 7 supports the reagent containers 1 by entirely supporting the housing 6 illustrated in FIG. 3. Further, the support member 7 has holes 8 into which the reagent supply ports 5 of the reagent containers 1 are fitted, and nozzles 9 are arranged in the holes 8 so that acute ends thereof are directed in an upward direction. When the housing 6 illustrated in FIG. 3 is set on the support member 7 illustrated in FIG. 4, the reagent supply ports 5 exposed from the housing 6 are fitted into the holes 8 so that the nozzles 9 are inserted into the nozzle penetration portions 5b. Further, the holes 8 each also have a function as a guide for controlling an introduction distance in the reagent container 1 for the nozzle 9 to prevent the nozzle 9 from entering the reagent container 1 excessively deeply or dropping off the reagent container 1.

Figure 5:
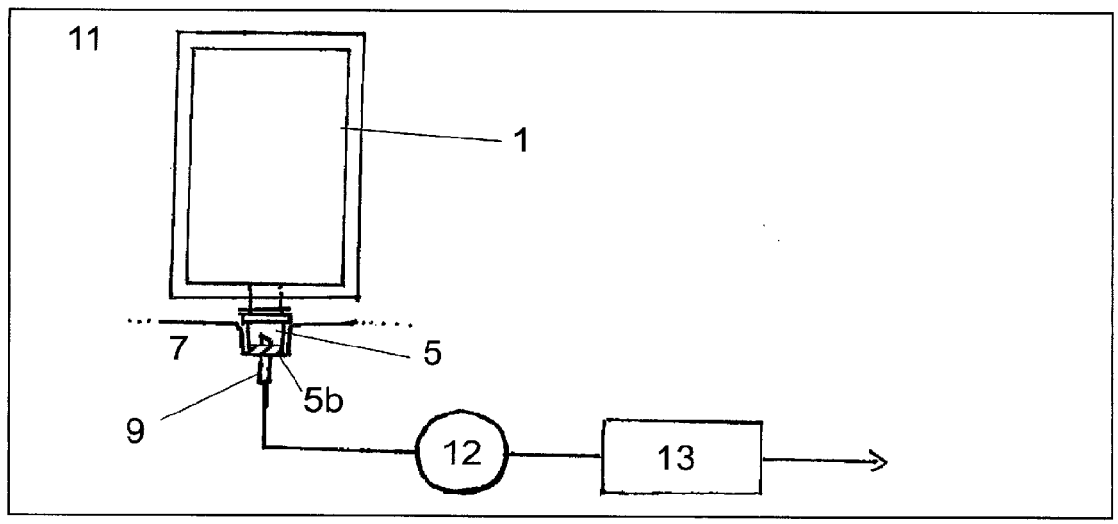
FIG. 5 is a schematic view of a reagent supply device connected to a sample analysis unit.

When the nozzle 9 is inserted into the reagent container 1 through the nozzle penetration portion 5b, the reagent is supplied from the reagent container 1. The reagent supply port 5 is located on a lower side of the reagent container 1, and hence the reagent in the container is caused to flow out of the container in a downward direction through the nozzle 9. FIG. 5 is a schematic view of one embodiment of a reagent supply device 11 according to the present invention, which is connected to a sample analysis unit. In FIG. 5, the reagent container 1 is supported on the support member 7 being a hole including the nozzle 9, and is arranged under a state in which the reagent supply port 5 is directed in a downward direction. The reagent in the reagent container is supplied from the nozzle 9, which is inserted into the nozzle penetration portion 5b of the reagent supply port 5, to a sample analysis unit 13 through a liquid feeder 12.

Example 2

Sample Analysis Device

Figure 6:
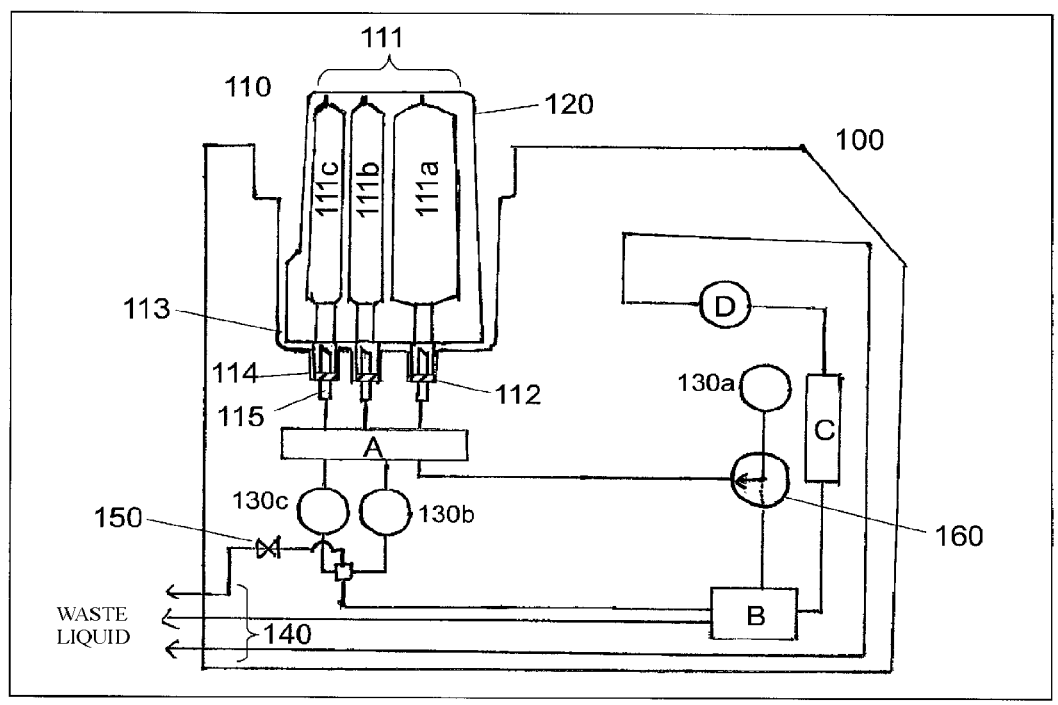
FIG. 6 is a schematic view of a blood sample analysis device.

FIG. 6 is a schematic view of a blood sample analysis device 100 based on liquid chromatography according to another embodiment of the present invention. The blood sample analysis device 100 has a reagent supply device 110 of the present invention built therein. Similarly to FIG. 4, in FIG. 6, a support member 113 of the reagent supply device 110 is formed on a body of the analysis device 100 for an analysis using the reagent supplied from the reagent supply device 110, and a housing 120 accommodating reagent containers is set on the support member 113. The housing 120 accommodates three reagent containers 111 each including a flexible container body. In the reagent containers 111, there are respectively filled a reagent being a solution for hemolyzing or diluting a blood sample and being a washing solution for washing a flow channel for the sample (solution 111a for hemolysis, dilution, and washing), and two kinds of eluents (111b and 111c). Each of the reagent containers 111 accommodated in the housing 120 is arranged under a state in which a reagent supply port 112 is directed in a downward direction.

The support member 113 has holes 114, and each of the holes 114 includes a nozzle 115 having an acute end directed in an upward direction. When the housing 120 is set on the support member 113, the reagent supply ports 112 of the reagent containers are fitted into the holes 114 so that the nozzles 115 are inserted into the containers 111 through nozzle penetration portions of the reagent supply ports 112. Thus, the reagents in the containers 111 can be flew out to the outside of the containers through the nozzles 115.

When the blood sample analysis device 100 is activated, the reagent, which is stored in each of the reagent containers 111, is supplied to a sample injection portion B or a chromatographic column C of the sample analysis device. A supply rate or amount of each of the reagents is controlled by each of pumps 130a to 130c installed for each of the reagents. The reagent that has been used for the analysis is collected as a waste liquid through a discharge-liquid flow channel 140.

The blood sample is set in the sample injection portion B. When the blood sample analysis device is activated, the solution 111a for hemolysis, dilution, and washing is supplied to the sample injection portion B. Then, the blood sample is hemolyzed and the hemolyzed sample is diluted. A predetermined amount of the diluted sample is injected into a flow of the eluents 111b and 111c from the sample injection portion. After that, the diluted sample is fed to the column C by the flow of the eluents 111b and 111c, and components to be detected are separated by the column and detected by a detection portion D.

REFERENCE SIGNS LIST 1 reagent container
2 container body
3 bag
4 outlet portion
5 reagent supply port (plug)
5a plug body
5b nozzle penetration portion
6 housing
7 support member
8 hole
9 nozzle
10 body of analysis device
11 reagent supply device
12 liquid feeder
13 sample analysis unit
100 blood sample analysis device
110 reagent supply device
111 reagent container
111a solution for hemolysis, dilution, and washing
111b eluent b
111c eluent c
112 reagent supply port
113 support member
114 hole
115 nozzle
120 housing
130a-130c pump
140 discharge-liquid flow channel
150 drainage valve
160 three-way valve
A deaeration unit
B sample injection portion
C chromatographic column
D detection portion

The invention claimed is:

1. A system, comprising:
    a reagent container comprising:
        a container body suitable for storing a liquid reagent, and
        a reagent supply port arranged on the container body; and
    a support member suitable for supporting the reagent container from below, so that the reagent supply port is positioned on a lower side of the container body,
    wherein the reagent supply port comprises a nozzle penetration portion, and
    wherein the nozzle penetration portion comprises a material having a Shore hardness of from A5° to A90°.

2. The system according to claim 1, further comprising a liquid feeder suitable for feeding the liquid reagent to a sample analysis unit.

3. The system according to claim 2, wherein the reagent container is arranged at a position higher than the sample analysis unit.

4. The system according to claim 1, wherein the support member comprises a nozzle, and the nozzle is arranged at a position corresponding to the nozzle penetration portion of the reagent container.

5. The system according to claim 1, wherein, when the reagent container is supported by the support member, the nozzle is inserted into the nozzle penetration portion of the reagent container.

6. The system according to claim 1, wherein the material having a Shore hardness of from A5° to A90° comprises an olefin-based elastomer or a styrene-based elastomer.

7. The system according to claim 1,
    wherein the reagent supply port comprises a plug body and the nozzle penetration portion, and
    wherein the plug body and the nozzle penetration portion are joined to each other at flanges thereof.

8. The system according to claim 1, further comprising a housing suitable for accommodating the reagent container in a uniformly-spaced arrangement.

9. The system according to claim 1, further comprising a housing suitable for accommodating the reagent container in a non-uniformly-spaced arrangement.

10. The system according to claim 8, wherein the support member supports the reagent container by supporting the housing.

11. The system according to claim 1, wherein the liquid reagent comprises a reagent suitable for liquid chromatography.

12. A sample analysis device, comprising:
the system of claim 1; and
a sample analysis unit.

13. The system according to claim 1, further comprising:
an outlet portion fixed to the container body and having a screw thread,
wherein the reagent supply port is threadedly engagable with the outlet portion.

14. A reagent container comprising:
a container body suitable for storing a liquid reagent;
an outlet portion fixed to the container body and having a screw thread; and
a reagent supply port arranged on the container body,
wherein the reagent supply port comprises a nozzle penetration portion,
wherein the nozzle penetration portion comprises a material having a Shore hardness of from A5° to A90°, and
wherein the reagent supply port is threadedly engagable with the outlet portion.

15. A reagent container comprising:
a container body suitable for storing a liquid reagent;
an outlet portion fixed to the container body and having a screw thread; and
a reagent supply port removably attached to the container body via the outlet portion,
wherein the reagent supply port comprises a nozzle penetration portion and a complimentary screw thread to the outlet portion, and
wherein the nozzle penetration portion comprises a material having a Shore hardness of from A5° to A90°.

* * * * *